United States Patent [19]

Little et al.

[11] 4,362,164

[45] Dec. 7, 1982

[54] ELECTRONIC PICK-UP DEVICE FOR TRANSDUCING ELECTRICAL ENERGY AND SOUND ENERGY OF THE HEART

[75] Inventors: Michael J. Little, Tarzana; Shi-Yin Wong, Santa Monica, both of Calif.

[73] Assignee: Hughes Aircraft Company, Culver City, Calif.

[21] Appl. No.: 186,074

[22] Filed: Sep. 11, 1980

[51] Int. Cl.³ .............................................. A61B 5/02
[52] U.S. Cl. ................................... 128/639; 128/715; 179/1 ST
[58] Field of Search ............... 128/639, 715, 773, 670, 128/671; 179/1 ST

[56] References Cited

U.S. PATENT DOCUMENTS

| | | | |
|---|---|---|---|
| 3,565,060 | 2/1971 | Sipple | 128/639 |
| 3,628,527 | 12/1971 | West | 128/639 |
| 3,848,582 | 11/1974 | Milani et al. | 128/639 |

FOREIGN PATENT DOCUMENTS

| | | | |
|---|---|---|---|
| 2555281 | 6/1977 | Fed. Rep. of Germany | 128/639 |
| 674744 | 7/1979 | U.S.S.R. | 128/639 |

OTHER PUBLICATIONS

DeLuce et al., "Pasteless Electrode . . . ", Med. and Biol. Eng. and Comput., 1979, May, No. 3, 17, 387–390.
Nilsson et al., "A Combined Microphone . . . ", Bio. Eng., vol. 8, No. 10, pp. 424–427, 431, Oct. 1973.

*Primary Examiner*—Lee S. Cohen
*Attorney, Agent, or Firm*—E. F. Oberheim; W. H. MacAllister; A. W. Karambelas

[57] ABSTRACT

A stethoscope transducer applicable as a conventional audio transducer and as a phonocardiogram transducer has a body which on one side mounts an electrode carrying chest bell and which on an opposite side mounts a conventional chest bell. A microphone and a rotor assembly are mounted in a cavity in the body. The microphone and earpiece connections on the body communicate through passages in the rotor assembly with the electrode carrying chest bell when the rotor assembly is in a first position and with the conventional chest bell when the rotor assembly is rotated to a second position. These are three electrodes, two being pickup electrodes which each occupy one quadrant of the chest bell rim in diametrically opposite positions. The third electrode is on the rim intermediate the pickup electrodes. The rim is of a non-wettable material providing a hydrophobic surface.

2 Claims, 14 Drawing Figures

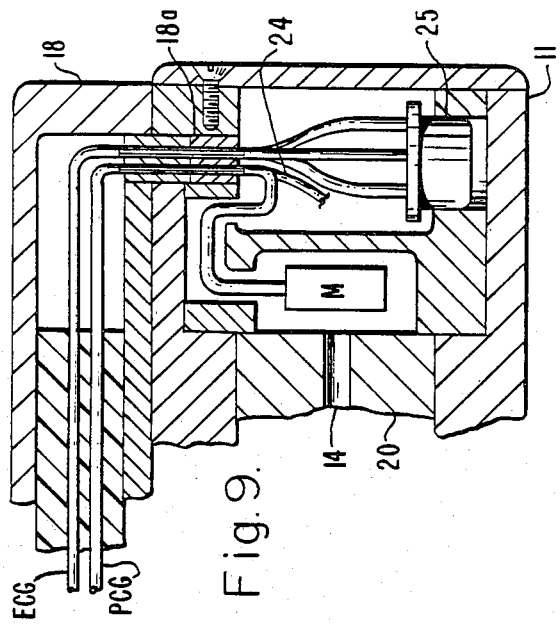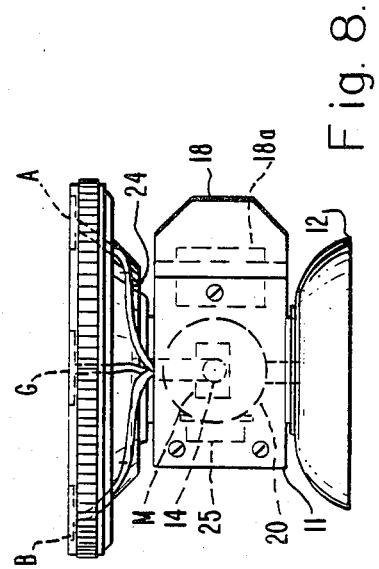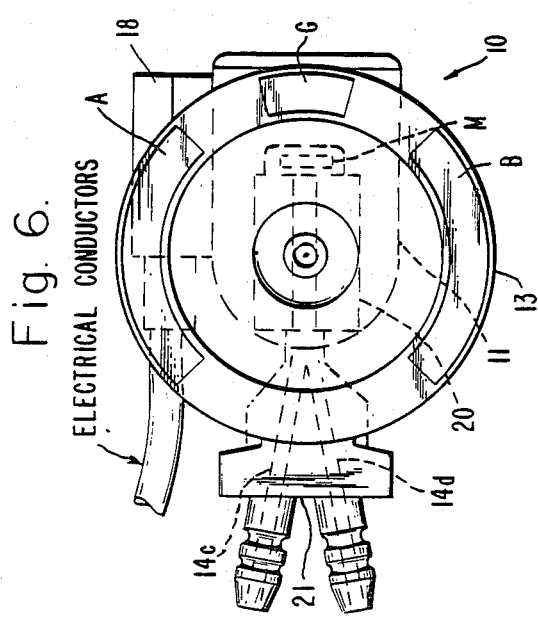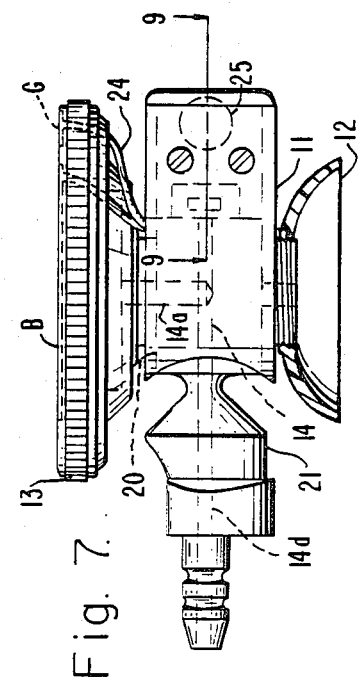

ELECTRONIC PICK-UP DEVICE FOR TRANSDUCING ELECTRICAL ENERGY AND SOUND ENERGY OF THE HEART

BACKGROUND OF THE INVENTION

1. Field of the Invention

This invention relates generally to an apparatus and a method of application of the apparatus for detecting heart activity in which provision is made for sensing both the electrical energy and the sound energy of the heart.

In a more particular aspect, this invention relates to a small pick-up device that may be hand held and its method of application to a body in the region of the heart, for detecting electrical and mechanical activity of the heart and simultaneously generating signals useful in producing displays, such as electrocardiograms depicting the elemental P, QRS, T and U characteristic of electrical heart activity, and also displays, such as phonocardiograms of the heart sound energy.

2. Description of the Prior Art Stethoscope

The stethoscope is an instrument used for the detection and pneumatic amplification of sound within the body or chest, particularly heart sounds, that are coupled to the ears of the user through air columns defined within flexible tubes coupled to a pick-up bell or diaphram. The stethoscope is an instrument which is easy and convenient to use, but it has low diagnostic value because it requires the ear to do sub-second interpretation of complex sounds. Additionally, the frequency of response of the ear is not well suited to detecting the sounds of the body.

Electrocardiogram

The generation of electrocardiograms involves the use of multiple electrodes selectively disposed in different position groupings on the body for detecting electrical signals generated by heart motion. The display can be either a recording on graph paper or a cathode ray tube or both or other display device such as a liquid crystal matrix. The information obtained is a measurement of the electro conduction system of the heart. When properly used, the electrocardiogram will indicate a heart attack in progress or any destruction of heart tissue resulting from a heart attack. Evaluation of an electrocardiogram frequently requires comparison with prior electrocardiograms of the same patient to indicate changes in the heart function. In general, equipment for producing electrocardiograms is cumbersome and time consuming. The predictive value of the electrocardiogram is low. The use of such equipment is limited primarily to specialists such as cardiologists.

Phonocardiogram

Equipment for producing phonocardiograms utilizes a pick-up responsive to heart sound energy for producing electrical signals which are amplified and utilized to produce a display on graph paper or on a cathode ray tube, or both, or other display device of the heart sound energy. The response of the system including the transducer and the reproduction equipment for producing the display is extremely important so that none of the sound characteristics are lost in acquiring the signal. Existing phonocardiogram equipment is cumbersome and time consuming to use. It is relatively expensive and is not widely used except by cardiologists because of the difficulty of interpreting the complex signal displayed.

Echocardiogram

Equipment for producing echocardiograms differs from equipment discussed hereinabove in the sense that ultra sonic wave energy which is broadcast is reflected by organs of the body. These reflections are displayed and when the equipment is properly used and the displays properly interpreted, it is possible to evaluate the condition of the tissue and its motion if any. Here again, the equipment is cumbersome and the process of producing the echocardiogram is time consuming. Use of the equipment is limited almost exclusively to cardiologists.

Special Devices

Efforts to improve and miniaturize heart electrical energy and heart sound energy transducers are reflected in the following patents:

U.S. Pat. No. 3,858,005

Stethoscope With Display; inventor Robert A. Marshall; patented 31 Dec. 1974.

The patentee Marshall has modified the chestpiece of a conventional stethoscope to include a small cathode ray tube. The amplified outputs of crystal pick-ups disposed on the diaphram of the stethoscope chestpiece are displayed on the cathode ray tube, which is said to be a display of the heart sounds as in a phonocardiogaph.

U.S. Pat. No. 3,182,129

Electronic Stethoscope; inventor W. B. M. Clark et al; patented 4 May 1965.

The patentee Clark et al, commenting on the shortcomings of prior art devices with respect to limitations in their range of frequency response, their ineffective amplification of the lower frequency sounds as well as the higher frequency sounds, and their cumbersome physical characteristics, describes a stethoscope in which the transistor amplified output of a diaphram stressed crystal element is coupled to a speaker element such as an earpiece of a conventional hearing aid. Charts and graphs are provided to depict the improvement provided by this arrangement over that of the conventional acoustic stethoscope.

U.S. Pat. No. 3,960,141

Electro Surgical and ECG Monitoring System; inventor Lee R. Bolduc; patented 1 June 1976.

The patentee Bolduc simultaneously monitors a patient's beat-by-beat heart signal during an electro surgical procedure using an electrode structure in which the ground and pick-up electrode are combined in a single electrode structure. The pick-up electrodes are arranged on the ground electrode in a manner to minimize interference from the use of the electro surgical unit on the patient. Using suitable displays, the surgeon is provided with a display of the patient's heart action.

U.S. Pat. No. 3,455,293

Stethoscope Device; inventor R. W. M. Bethune; patented 15 July 1969.

The patentee Bethune utilizes the metal chestpiece rim of a conventional stethoscope as one electrode element of an electrocardiogram display device. In accomplishing this, one of the ECG leads is connected to a metal face of the stethoscope chestpiece. The heart sounds are conventionally acoustically coupled from the chestpiece to the earpiece of the stethoscope through flexible tubing.

U.S. Pat. No. 3,682,161

Heart Beat Transducer for a Monitoring Device; inventor Vernon F. Alibert; patented 8 Aug. 1972.

Using a principle similar to the patentee Clark et al above, the patentee Alibert mounts a plurality of piezoelectric crystal elements on a flexible element which is flexed by a diaphram element mounted in the transducer head and adapted to contact the body of a patient. The electrical output of the piezoelectric crystal elements is coupled to a suitable utilization device.

SUMMARY OF THE INVENTION

The prior art discussed hereinabove includes arrangements for sensing either electrical or sound energy of the heart using separate transducers. Only the patent to Bethune of the items cited, attempts to combine electrical and sound energy sensing of the heart, however, the chestpiece of Bethune is not a self-contained unit capable of producing respective electrical signals in response to electrical and sound energy activity of the heart and the sound energy is coupled only to the earpiece.

Recognizing a need for improvement in arrangements for displaying heart activity and particularly for providing a small portable stethoscope equipment including displays which are an aid in "on the spot" diagnostic efforts, this invention provides an improved stethoscope chestpiece, usable with a small portable display, that is approximately the same size as the conventional stethoscope chestpiece but which is a self-contained transducer of electrical and sound energy activity of the heart, producing separate electrical signals of such activities. One signal being applicable in producing a display corresponding to an electrocardiogram (ECG) and the other signal being applicable in producing a display corresponding to a phonocardiogram (PCG) and annotated by the R wave of the electrocardiogram. The improved chestpiece also conventionally transmits heart sound energy via the air columns in the flexible tubes coupled to the earpieces.

The production of the separate but interrelated electrical signals is accomplished in the disposition of a plurality of electrodes in spaced positions insulated from one another on an end face of the chestpiece bell for picking up a signal pattern representing the conventional three-lead ECG when the electrodes are in contact with the skin of a patient, and, in the disposition of a sound energy transducer, such as a microphone, in the air column of the chestpiece to respond to air pressure variations characteristic of heart sound energy, for producing an electrical signal pattern representing a PCG.

The electrodes are spaced to permit application of the chestpiece, for sensing heart acitivity, on the patient's chest in the region of the heart. Movement over the chest when the chestpiece is connected to the display equipment, may be made to a position in which adequate signal strength is detected and in which the signal pattern resembles the conventional three-lead electrocardiogram signal depicting the P-wave, the QRS-wave, the T-wave and the U-wave. This ECG signal is useful both as a diagnostic aid and the QRS-wave, also called the R-wave, is useful in annotating the sound energy signal, that is, the phonocardiogram signal, for display purposes.

Unlike the electrodes of prior art electrocardiogram equipment, the electrodes of this improved chestpiece are directly appicable to the skin of the patient to pick up electrical energy. The conductive jel ordinarily used in achieving electrical contact and providing a stable electrical conductive path between the skin of the patient and the electrode, is not needed, eliminating delays in the use of the chestpiece. This is accomplished in the use of an electrode metal such as silver, including a redox couple of the metal and a skin surface chemical, such as the chlorine in sodium chloride and/or potassium chloride, to produce silver chloride which is insoluble in fluids commonly present on the body, to provide a conductive path between the skin of the patient and the electrode. With such an arrangement, small current flows will not significantly change the concentration of chloride ions in the current path, maintaining a relatively stable potential between the electrode and the body.

The low current is assured in this improved chestpiece in the provision of an electrode circuit having a high input impedance. Whereas prior art electrode circuits may have input impedances of the order of $10^6$ ohms. The input impedance of the electrode circuit of this improved chestpiece is about $10^{13}$ ohms.

BRIEF DESCRIPTION OF THE DRAWINGS

The objects and advantages of this invention will be better understood from a study of the following specification when considered in conjunction with the accompanying drawings in which:

FIG. 2b is a phonocardiogram tracing for a normal heart positioned in timed relationship with respect to the electrocardiogram of FIG. 2a.

FIGS. 6, 7 and 8 are respectively plan, elevational, and end views of the improved chestpiece.

FIG. 9 is an enlarged sectional view taken on the line IX—IX of FIG. 7.

DESCRIPTION OF A PREFERRED EMBODIMENT

Figure 1:
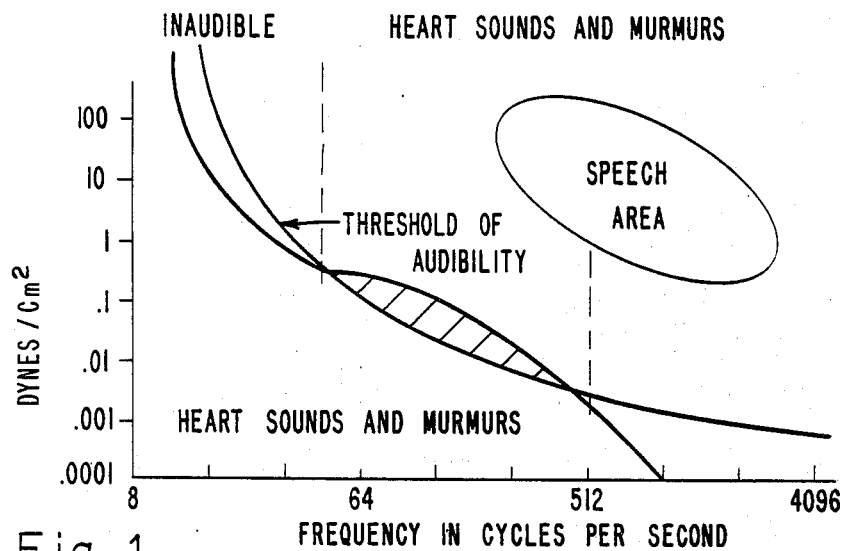
FIG. 1 plots the signal domain of heart sounds and the threshold of audibility of the human ear, depicting the approximate region of speech sounds for comparison.

In the analysis of heart activity and in the diagnosis of abnormalities in heart function, it is important that the initial examination produce as much information as possible in enabling the examining physician to correctly diagnose a specific malfunction. Frequently, preliminary or initial examinations are made in circumstances in which access to elaborate diagnostic equipment is not possible and of necessity the conventional physicians' stethoscope is utilized in attempting to detect body sounds particularly those of the heart for diagnostic purposes. In the conventional physicians' stethoscope, heart sound energy is coupled from the chestpiece to the earpieces via the air columns in the flexible tubes. It will be seen by reference to FIG. 1 that the overlap between the curve depicting the lower threshold of audibility of a normal human ear and the curve defining the signal domain of heart sounds and murmurs covers only a very small part of the heart sound energy spectrum useful in diagnosing problems associated with the heart. For instance, compare this with the depicted signal domain of normal speech which lies entirely within the curve of the lower normal threshold of audibility of the human ear.

Figure 2A:
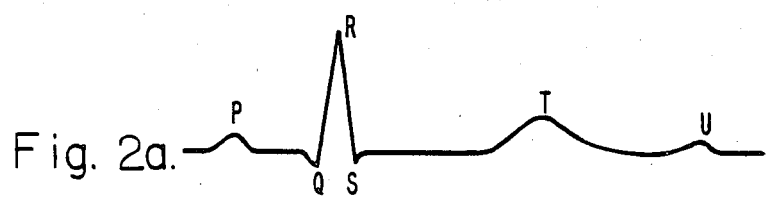
FIG. 2a is a curve or a trace resembling a conventional three-lead electrocardiogram for a normal heart.
Figure 2B:
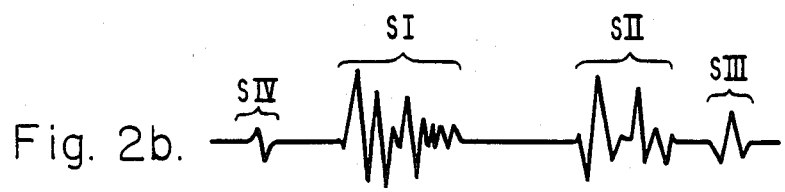

Attempts to improve heart sound detection are represented in some of the patents discussed hereinabove particularly those in which electronic amplification of the heart sound is employed to increase the heart sound energy level for detection by the human ear. But such approaches, if productive of improvement in the detection of heart sound, are inadequate in that the detected heart sound activity is unrelated to the electrical activity of the heart which information is important in relating the sound which is heard to the specific phase of heart activity and hence the source of the sound which is heard. FIG. 2a and 2b graphically depict the relationship of an electrocardiogram trace and a phonocardiogram trace for a normal heart. Now the heart sounds SI-SIV are depicted in proper relationship with the waveforms of the electrocardiogram and can be interpreted in that respect so that the sound which is heard (or which is displayed) is clearly related to the functional cycle of the heart as depicted by the electrocardiogram. Thus, in the use of heart sound energy or in the use of a phonocardiogram trace or both in diagnosing an abnormality of the heart function, it is important that the detected heart sound energy, however it may be presented for evaluation, is related to the electrocardiogram. Usually the QRS-wave, sometimes called the R-wave, is employed to annotate the signal of heart sound energy. In general, the heart sounds contain specific information with respect to the condition of the heart. If a transducer is used capable of transducing the range of heart sound frequencies, it is possible to produce a display that is a phonocardiogram which accurately characterizes otherwise undetectable malfunctions of the heart. When properly annotated by the R-wave of the electrocardiogram, a properly displayed phonocardiogram is useful in identifying the source and the character of the malfunction of the heart.

Figure 3A:
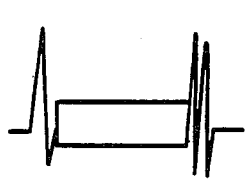
FIGS. 3a and 3b are textbook type illustrations of phonocardiograms depicting systolic and diastolic murmurs respectively.
Figure 3B:
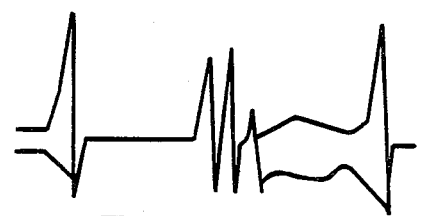

Textbook characterizations of phonocardiograms depicting certain malfunctions of the heart are illustrated in FIGS. 3a and 3b. FIG. 3a depicts a systolic murmur and FIG. 3b depicts a diastolic murmur. Such idealized versions of heart malfunction are difficult to produce in practice and importantly require a transducer responsive to the essential range of heart sound frequency for producing a signal pattern faithfully representing the heart sound energy coupled into the transducer. Still further inovative display techniques are required such as described in a co-pending application entitled "Method and Improved Phonocardiograph Apparatus for Analyzing Heart Activity"; inventors Shi-Yin Wong et al and filed on the same date as this application.

Displays approaching the idealized textbook versions are achieved in symmetrical displays of the full wave rectified phonocardiogram signal annotated by the R-wave of the electrocardiogram signal.

A better understanding of this invention may be had be reference to said co-pending application, the subject matter of which is incorporated in its entirety herein by reference thereto. For present purposes, however, reference may be had to FIG. 4 herein for a brief description of a chestpiece for transducing both electrical and heart sound energy and a block diagram of a display system associated therewith for displaying both the electrical and the heart sound energy signals. Here the chestpiece 10 comprises a body portion 11. Respective bells 12 and 13 are mounted on opposite sides of the body portion 11. In use, the open ends of the these bells are selectively positioned on the body of a patient. Passages 14, the open end of one of which is shown substantially centrally of the bell 13 within the body portion 11, communicate with flexible tubes 15 which connect with the earpieces (not shown) of the stethoscope. The structure thus far described characterizes the conventional stethoscope. This improved stethoscope is provided with a plurality of electrodes mounted upon one of the bells, here indicated as the larger of the two bells 13. The electrodes are identified A, B and G disposed in circumferencially spaced positions on the end face of the bell 13. The bell 13 is formed from an insulating material, of a type to be described, to provide electrical isolation of the electrodes one from the other.

As will be described at a later point, the electrodes are of a metal which will permit direct application of the electrodes to the skin of a patient without the need for a conductive gel. A microphone M is located within the body portion 11 of the stethoscope in a position to be subject to air pressure variations in the passage 14. Electrical signals detected by the electrodes are coupled to a high input impedance amplifier (not shown) within the body portion 11 of the stethoscope. These amplified electrical signals together with signals from the microphone are coupled out of the stethoscope by means of a connector element 18 in separate circuits, one of which is identified as ECG input, and the other identified as PCG input denoting the electrocardiogram and the phonocardiogram inputs respectively.

Figure 4:
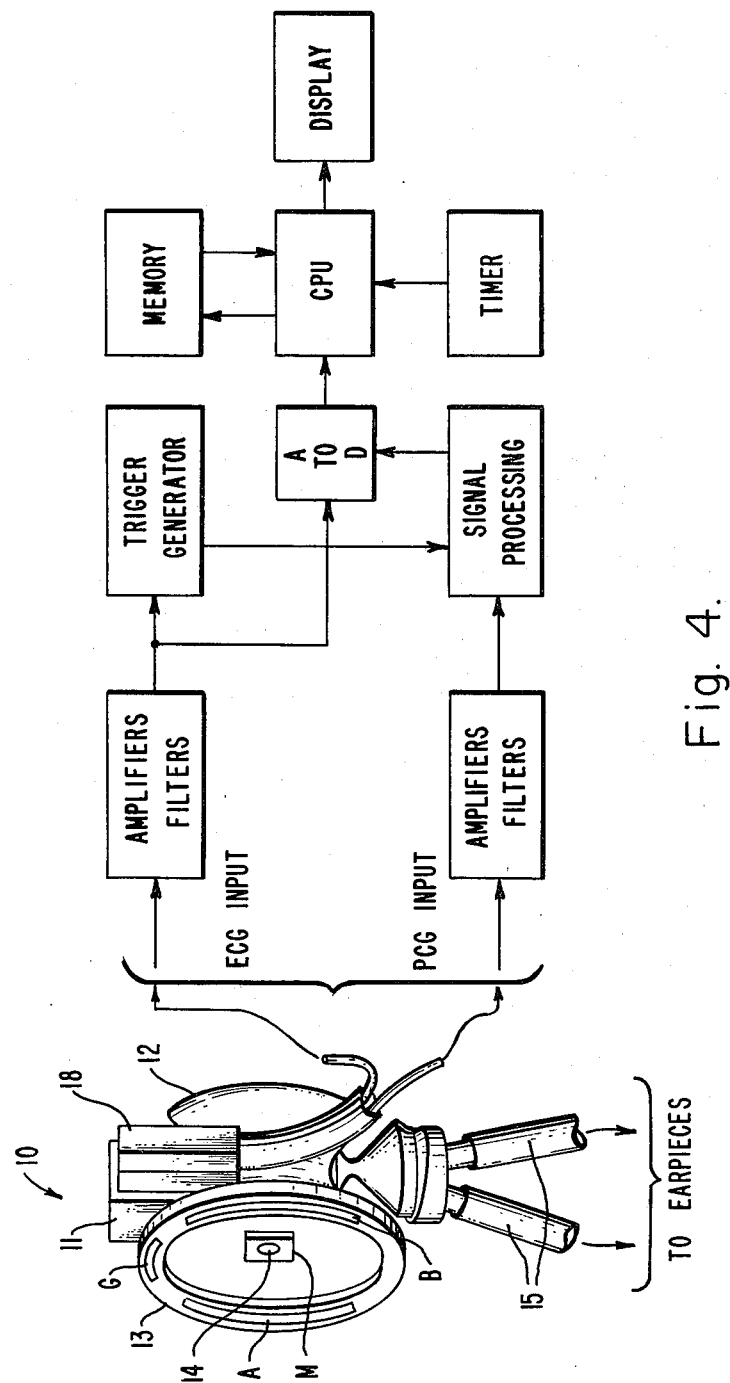
FIG. 4 shows a perspective view of a chestpiece embodying the principles of this invention together with a diagrammatic illustration of a type of display system to which the chestpiece may be coupled for displaying the electrocardiogram and phonocardiogram signals.

The display system illustrated in elementary block diagram form in FIG. 4 embodies the principles of that in the referenced co-pending application. The phonocardiogram input is amplified and filtered in circuits which may also include automatic gain control. The phonocardiogram signal is then coupled inputwise to a signal processing circuit in which the signal is full-wave rectified. A trigger generator circuit responsive to the R-wave of the electrocardiogram signal has an output coupled to the signal processing circuit for the purpose of annotating the full-wave rectified phonocardiogram signal. The annotated rectified phonocardiogram signal is coupled to an analog-to-digital converter. The output of which is coupled input wise to a central processing unit providing display mode control, that is, either "freeze" or "run" modes of display and wherein the phonocardiogram signal, after conversion to analog form, is "symmetrized" in oscillator controlled display circuits by alternately switching the inverted and normal annotated full-wave rectified phonocardiogram signal into the input circuits of the display device for simultaneous symmetrical display. By this expedient, displays characterizing the envelope displays of FIGS. 3a and 3b, for example, are achieved to provide readily recognizable displays of particular coronary conditions. Circuit details for achieving such a display may be had by reference to said co-pending application.

Figure 5:
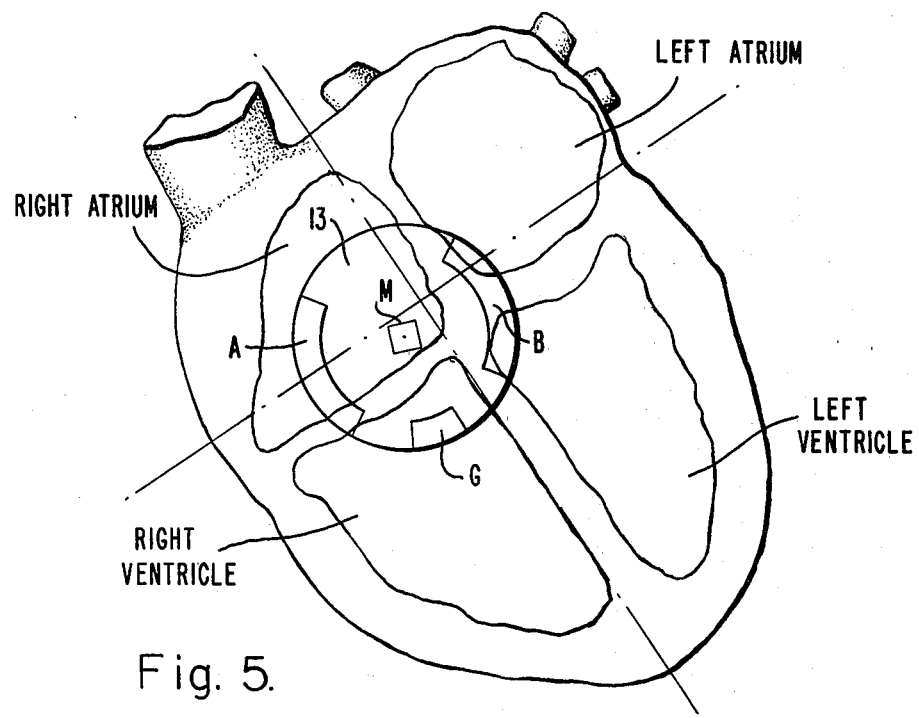
FIG. 5 illustrates the chestpiece positioned over the heart.

FIG. 5 illustrates the three electrode electrical signal pick-up bell 13 disposed over the heart. The position of the electrical pick-up over the heart is not to be regarded as a preferred position but merely as an illustration of one application of the stethoscope to the body. With reference to FIG. 4 it will be seen that the electrocardiogram signal is coupled through the analog-to-digital converter to the central processing unit from which it is coupled to the display. With such an arrangement the stethoscope may be moved over the heart to produce a display which best characterizes the conventional three-lead electrocardiogram. Three-lead electrocardiogram as here used is intended to mean that display normally achieved with conventional ECG equipment with leads coupled to the left and right arms respectively and the ground lead coupled to the left leg. Thus, in FIG. 5 the electrode A corresponds to the electrode connected to the patient's right arm and the electrode B corresponds to the electrode connected to the patient's left arm, while the ground electrode corresponds to that electrode connected to the patient's left leg. The display which is achievable resembles the conventional trace depicted in FIG. 2a herein and is useable in conjunction with the phonocardiogram for diagnostic purposes. As described in the referenced co-pending application, the electrocardiogram and phonocardiogram displays may be selectively switched to the display device, or, in the alternative may be simultaneously displayed depending in part upon the size of the display area and in part upon the size of the display required for specific diagnostic purposes.

As discussed herein above, the stethoscope is applied directly to the skin of the patient. That is, there is no preliminary preparation of the skin of the patient as by means of the conductive gel using conventional electrocardiogram electrode structures. The utility of the equipment is significantly improved in the elimination of the conductive gel requirement in that the equipment is usable in almost any circumstances for examining a patient. In this respect, also note is made of the fact that the stethoscope chestpiece does not need to be enlarged in any way to accomodate the additions which have been made. It is usable in a manner to which the physicians are accustomed and, as described in said co-pending application, the circuits and displays are sufficiently small to be carried upon the person of the physician for "on the spot" use and diagnosis of a patient's heart condition. Significantly improving the amount and quality of information available to the physician aiding him in making an accurate diagnosis.

FIGS. 6, 7, 8, 9 and 10 illustrate details of the stethoscope chestpiece. The body portion 11 of the stethoscope chestpiece 10 is provided with a cylindrical cavity for receiving a cylindrical rotor 20 which is rotatable between two detent positions which are 180° apart. The rotor 20 is provided with the internal passages 14 referred to in the description of FIG. 4. One part of which extends axially through the rotor in communication with a radial passage 14a extending therefrom, on one side only, of the central passage. The passage 14 divides into two passages 14c, 14d in an external fitting 21 which is connected to or forms part of the rotor 20. The passages 14c, 14d terminate in respective hose fittings extending from the fitting 21 for receiving the flexible tubes normally coupled to the earpieces (not shown). With the construction thus far described, it will be seen that by rotating the cylindrical rotor 20 between its two detent positions, the radial passage 14a may be connected either with the corresponding passage in the chestbell 12 or in the chestbell 13 which latter position is the position illustrated. Thus, heart sound energy is communicated through the central opening in either of the chestbells into the passage 14a and thence through the passage 14 and via the passages 14c, 14d to the air columns in the flexible hoses coupled to the earpieces, thus conventional audio stethoscope operation is provided.

While the electrodes may be disposed on either of the chest bells, they are here illustrated as disposed upon the larger of the two chest bells. These electrodes are circumferentially dimensioned to occupy roughly one quadrant of the circumferential dimension of the chest bell in diametrically opposite positions. The ground electrode is disposed in the rim of the chest bell between the corresponding ends of the electrodes A and B. It is here shown as a smaller electrode than either of the electrodes A and B since it is not an electrical energy pick-up electrode. Its size may be varied depending upon requirements and the space between the ends of the ground electrode and the two pick-up electrodes A and B is such as to minimize short circuiting between the ends of the adjacent electrodes that may result from the accumulation of body fluids in the electrode end gaps when the chestpiece is in use.

Figure 12:
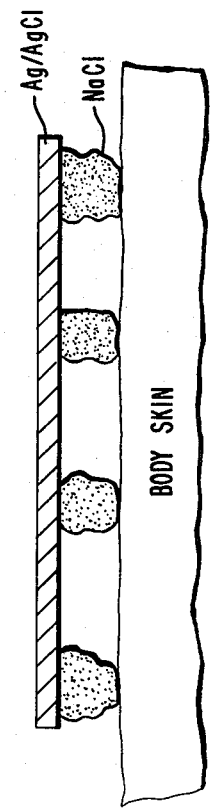
FIG. 12 is a cross-sectional view useful in understanding the electro chemical coupling between a chestpiece electrode and the skin of the body.
Figure 10:
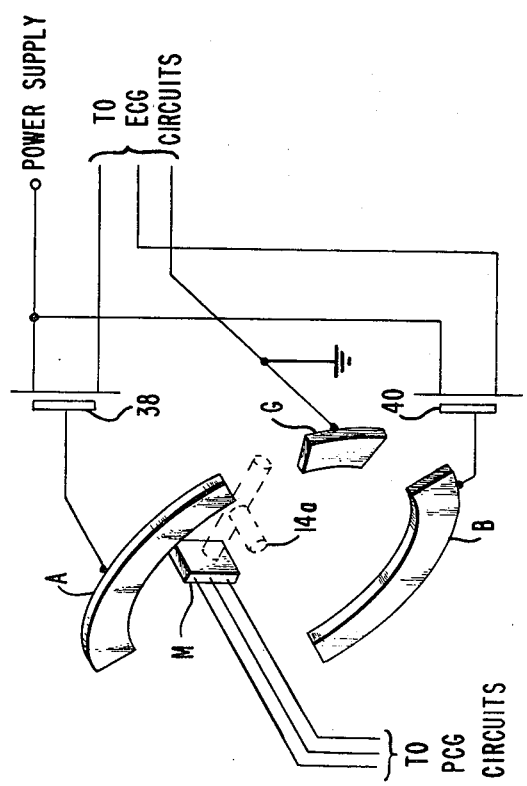
FIG. 10 diagrammatically depicts the electrical circuits of the improved chestpiece.

The body portion of the chest bell 13 is of an insulating material which is preferably a non-wettable material providing a hydrophobic surface so that moisture will not adhere and wet the surface to short the electrodes in a conductor bridge. The electrodes are relatively thin and may be recessed into the rim of the chest bell 13. The thickness of the electrode and its mode of attachment is preferably such as to minimize the possibility of peeling of the electrode in ordinary usage. There are a number of materials that may be used for the metal electrodes. These include, by way of illustration but not limitation, platinum, gold and silver. The requirement is that the metal selected for the metal electrode be capable of forming a redox couple with a chemical commonly found on the surface of the body and that such redox couple be insoluble in the presence of body fluids. Sodium chloride is such a body chemical and readily forms the redox couple of silver-silver chloride (Ag-AgCl). Electrodes of this type may be formed in a conventional electro chemical process in which a silver electrode is immersed in a sodium chloride bath and subjected to electro chemical reaction. The result is a silver-silver chloride (Ag-AgCl) electrode which contains a chloride ion concentration which will not change in body surface contact in the presence of small currents while maintaining stable potential between the electrode and the skin of the body. With reference to FIG. 12, an attempt is made to present a picture of an electrode relationship to the skin of the body of the patient. Here, the predominate chemical, sodium chloride (NaCl) is depicted in globule form in an exaggerated electro chemical contact relationship between the electrode and the skin of the patient. The assumption is made here that sodium chloride is the predominate body surface fluid and no attempt has been made to pictorially introduce the presence of other body surface chemicals. Unlike the conventional ECG electrode application to the skin of a patient, no conductive gel containing sodium chloride is contemplated in this relationship. The chloride or chlorine ions present and required in the electro chemical relationship between the electrode and the skin of the patient existing in sufficient stable concentration in the silver chloride concentration on the electrode itself, not requiring reliance upon the presence of sodium chloride in sufficient abundance in the presence of a conductive gel and/or body surface fluids. Thus, the use of a metal for the electrode having a redox couple of the metal and a predominate body chemical provides an arrangement permitting direct contact of the electrode with the skin of the body with sufficient ion concentration, such as chloride ions, to establish an electro chemical contact whereby body currents may be picked up.

Small currents will not change the concentration of chloride ions in the conductive path. Thus, a stable potential between the electrode and the body may be maintained. Small currents are assured, in this instance, in the provision of high input impedance circuits to which the electrodes are connected. As will be seen by reference to FIG. 10, the electrodes A and B are connected to the gate electrodes of respective transistors 38 and 40 which may be field effect transistors. The source electrode of each of these transistors is connected to a power supply whereas the drain electrode, together with a circuit from the ground electrode, are connected to the electrocardiogram (ECG) circuits. The field effect transistors present high input impedances as seen from the electrodes A and B and only very small currents flow in these electrode circuits. The leads coupled between the electrodes A and B and the gate electrodes of the field effect transistors 38 and 40 are kept as short as possible and are shielded to minimize stray capacitance coupling, to limit capacitance to avoid bandwidth limitations and to minimize any physical contact with the wires that might generate charge motions which could be picked up by the display.

Physically, these goals are achieved in an arrangement as seen in FIG. 9 wherein the field effect transistors 38 and 40 together with amplifiers for the signals of the microphone M are housed in an amplifier package 25 which is secured in a cavity in the body portion 11 of the stethoscope. As will be seen in FIG. 7, conductors 24 from the electrodes enter the body portion 11 through a suitable opening at the base of the chest bell 13. These leads, as seen in FIG. 9, within the body portion 11 are coupled to a multiple terminal electrical connector 18a through which connection is made to the amplifier 25 and from which connection is made to the output leads in the electrical connector housing 18. While it is evident that the use of a metal body portion 11 provides shielding for the wires, individual wire shielding is nontheless recommended to minimize stray coupling and to stiffen the cables to increase their resistance to shock in the event of rough handling of the stethoscope chestpiece.

The phonocardiogram signals are generated by the microphone M, here depicted in a cavity in the body portion 11 in a position confronting the open end of the passage 14 in the rotor element 20. In this position, the microphone is subject to air pressure variation when the rotor is coupled to either of the chest bells 12 or 13. The microphone may be any conventionally obtainable microphone. That which has been successfully used is Tibbits Industries of Camden, Maine, Model #153X/989. The microphone wires are also shielded and coupled through the amplifier package 25 to the output leads through the multiple terminal connector block 18a.

Figure 11:
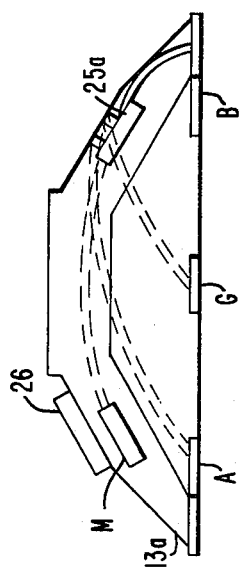
FIG. 11 is a cross-sectional view of a modified chestpiece bell.

An alternative construction eliminates the need for an electrical cable such as that at the connector housing 18 for coupling the electrical signals from the electrodes and the microphone to the display circuits. A cross-section of a chest bell 13a is illustrated in FIG. 11 depicting the electrodes A, B and G in the body contacting rim of the chest bell and schematically depicting the electrical conduction connection of the electrodes to an amplifier 25a which may be moulded in the chest bell as it is formed. Similarly, connections from the microphone M to the amplifier package 25a are schematically depicted. The amplifier 25a has internal connections (not shown) with a transmitter 26 provided to broadcast the electrocardiogram and phonocardiogram signals to a local display and/or recording unit.

Thus, this invention provides a stethoscope apparatus and a method of application for detecting heart activity providing for sensing both the electrical energy and sound energy of the heart in which the stethoscope chestpiece is a small hand-held device generally of the same size and configuration as that which the physician is accustomed to using, which is directly applicable to the skin of the patient without any special preparation of the patient's skin, for picking up electrical signals from the body of the patient, for example, in the region of the heart which are useful in producing electrocardiograms of the patient's electrical heart activity and at the same time, for responding to the heart sound energy for producing electrical signals useful in the production of phonocardiograms of heart sound energy. The stethoscope increases the information at the physicians' disposal increasing the potential for accuracy in "on the spot" diagnostic efforts.

Although specific presently preferred embodiments of this invention have been disclosed, it will be apparent to those skilled in the art that many other variations involving the substitution of materials, the rearrangement of parts and the like may be had without departing from the spirit and scope of this invention.

We claim:

1. Apparatus including a stethoscope chestpiece, comprising:
   a stethoscope body portion;
   a chest bell having a base secured to said body portion and having a rim defining the open end of said chest bell, said chest bell being of electrical insulating material which is non-wettable providing a hydrophobic surface on said rim;
   three metal electrodes disposed on said rim, two of said electrodes being electrical current pickup electrodes which are each circumferentially dimensioned to occupy substantially one quadrant of said rim in diametrically opposite positions on said rim and the third being a ground electrode intermediate said pickup electrodes on said rim and which is smaller than said pickup electrodes, said metal electrodes each being capable of forming a redox couple of the metal and a chemical commonly found on the surface of the skin;
   said body portion having a passage therein opening through the base of said chest bell;
   a microphone supported in said passage; and
   utilization circuits electrically coupled to said electrodes and said microphone and including high input impedance circuit elements individually coupled to said pickup electrodes to be controlled thereby.

2. A stethoscope transducer applicable as a conventional audio transducer and as a phonocardiogram transducer, comprising:
   a body portion defining a cavity including a cylindrical portion and having a pair of chest bells mounted thereon in substantially opposite positions, said chest bells communicating with said cavity through passages in said body portion extending radially of said cylindrical portion, each of said chest bells having a rim;

a rotor assembly having a cylindrical section rotatably disposed in said cylindrical portion of said cavity for rotatable movement between two positions and having two passages therein, one passage being a central passage extending centrally, axially through said cylindrical section of the rotor assembly and the other passage being a radial passage extending on one side only from said central passage, which radial passage couples said central passage with one of said body portion passages in each of said two positions, said rotor assembly having an external section, said central passage communicating with said cavity in said body portion at the end of said rotor assembly opposite said external section and dividing into two passages in said external section for receiving stethoscope earpiece connections;

electronic circuits in said body portion;

spaced electrodes on the rim of one of said chest bells electrically coupled to said electronic circuits for picking up electrical signals produced by heart action and useful in producing electrocardiograms when said electrodes are in contact with the body in the vicinity of the heart; and a microphone disposed in said cavity in said body portion at said end of said rotor assembly opposite said external section to communicate with one of said chest bells in each position of said rotor assembly through said central axial and radial passages of said rotor assembly;

when said radial passage of said rotor assembly communicates with said one chest bell, said stethoscope transducer simultaneously produces electrical signals of the electrical activity of the heart and electrical signals of the heart sound activity by said microphone responsive to air pressure variations in said passages and said cavity, said electrical signals being useful in producing a phonocardiogram annotated by the electrical activity signal of the heart, and also communicates said air pressure variations to said divided air passages in said external section of said rotor assembly for use in audible heart signal detection and interpretation, and, when said radial passage of said rotor assembly communicates with the other of said chest bells, said stethoscope transducer simultaneously produces electrical signals of heart sound activity of said microphone for phonocardiogram display and communicates said air pressure variations to said divided air passages for audible heart signal detection and interpretation.

* * * * *